United States Patent
Larsson et al.

(10) Patent No.: US 6,723,066 B2
(45) Date of Patent: Apr. 20, 2004

(54) BREASTPUMP WITH UNIVERSAL HOOD BASE AND INTERCHANGEABLE SUCTION HOODS

(75) Inventors: Karl O.A.H. Larsson, Lindenweg (CH); Beat J. Moser, McHenry, IL (US); Andy Greter, Guntenbühl (CH); David A. Bates, Libertyville, IL (US); Brian H. Silver, Cary, IL (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 10/054,537

(22) Filed: Jan. 22, 2002

(65) Prior Publication Data

US 2002/0062103 A1 May 23, 2002

Related U.S. Application Data

(62) Division of application No. 09/450,404, filed on Nov. 29, 1999, now Pat. No. 6,387,072.
(60) Provisional application No. 60/111,895, filed on Dec. 10, 1998.

(51) Int. Cl.[7] ................................................. A61M 1/06
(52) U.S. Cl. ....................................................... 604/74
(58) Field of Search .............................. 604/74, 73, 48

(56) References Cited

U.S. PATENT DOCUMENTS

| | | | |
|---|---|---|---|
| 3,822,703 A | 7/1974 | Davisson | 128/281 |
| 4,680,028 A | 7/1987 | Stuart | 604/74 |
| 4,772,262 A | 9/1988 | Grant et al. | 604/74 |
| 4,794,915 A | 1/1989 | Larsson | 128/64 |
| 4,813,932 A | 3/1989 | Hobbs | 604/74 |
| 4,857,051 A | 8/1989 | Larsson | 604/74 |
| 4,929,229 A | 5/1990 | Larsson | 604/74 |
| 4,950,236 A | 8/1990 | Wilson | 604/74 |
| 5,049,126 A | 9/1991 | Larsson | 604/74 |
| 5,100,406 A | 3/1992 | Panchula | 606/74 |
| 5,258,041 A | 11/1993 | Guire et al. | 623/66 |
| 5,749,850 A | 5/1998 | Williams et al. | 604/74 |
| 5,776,177 A | 7/1998 | MacWhinnie et al. | 607/108 |
| 5,885,246 A | 3/1999 | Ford | 604/74 |
| 5,897,580 A | 4/1999 | Silver | 607/108 |
| 5,902,293 A | 5/1999 | Liu | 604/313 |
| 5,941,847 A | 8/1999 | Huber et al. | 604/74 |

Primary Examiner—Brian L. Casler
Assistant Examiner—Jeremy Thissell
(74) Attorney, Agent, or Firm—Baniak Pine & Gannon

(57) ABSTRACT

A breastpump is provided with a universal suction hood base that can be used with a set of different shields. An improved shield is further disclosed which is more flexible and conforms more readily to the breast, and also provides massage.

14 Claims, 2 Drawing Sheets

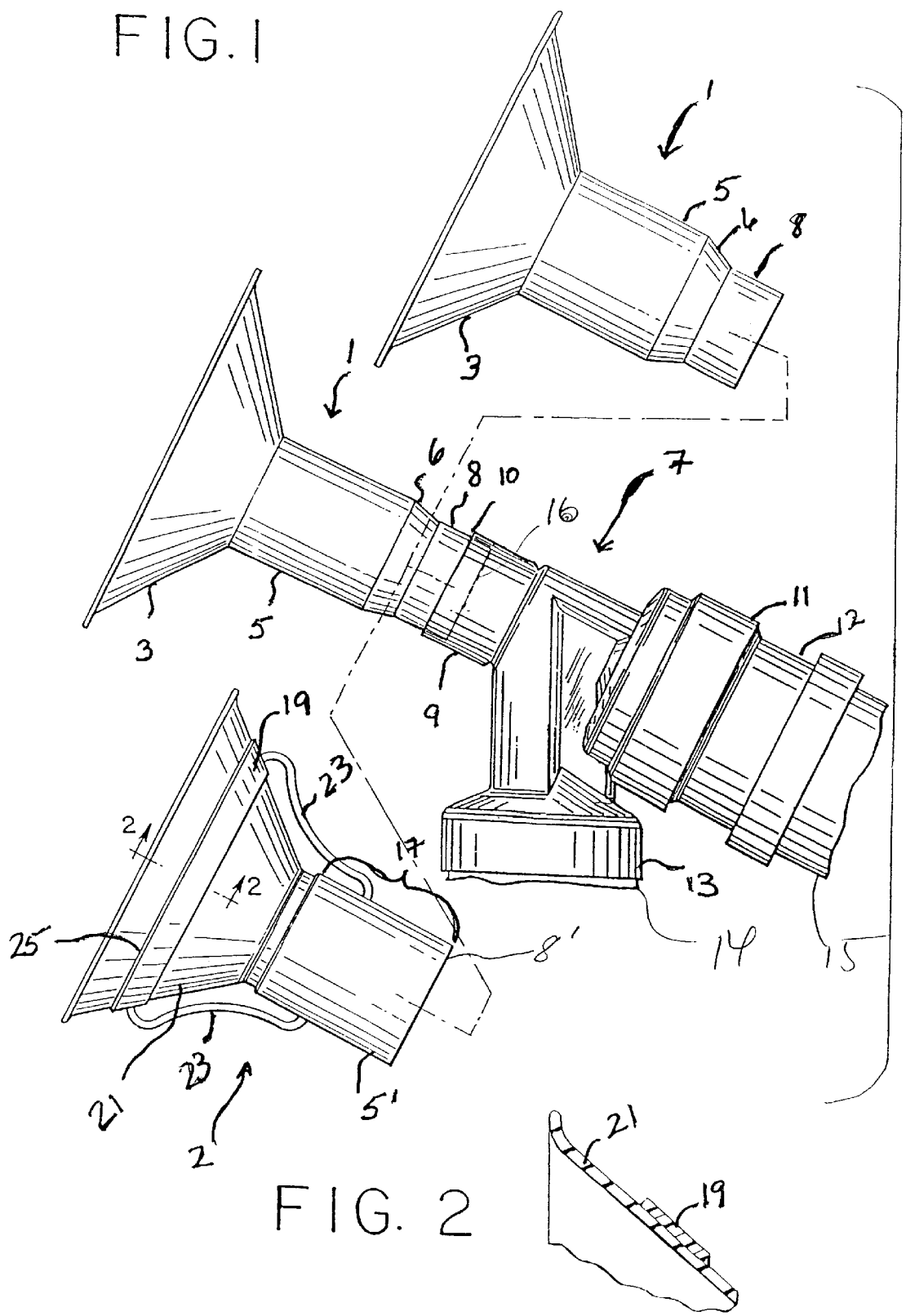
FIG. 1
FIG. 2
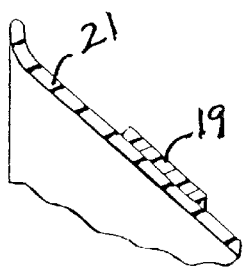

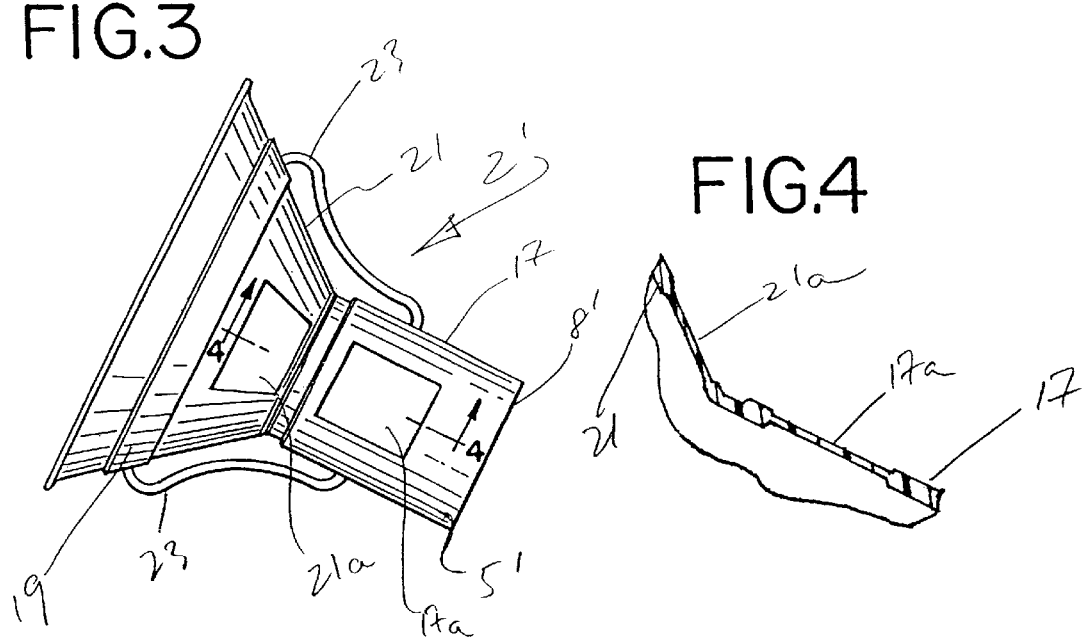
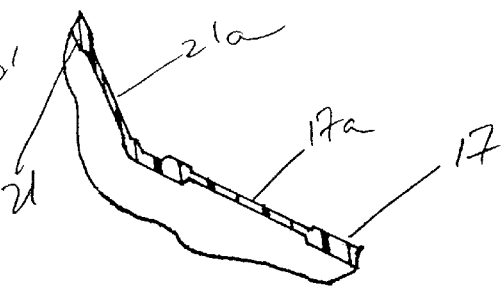
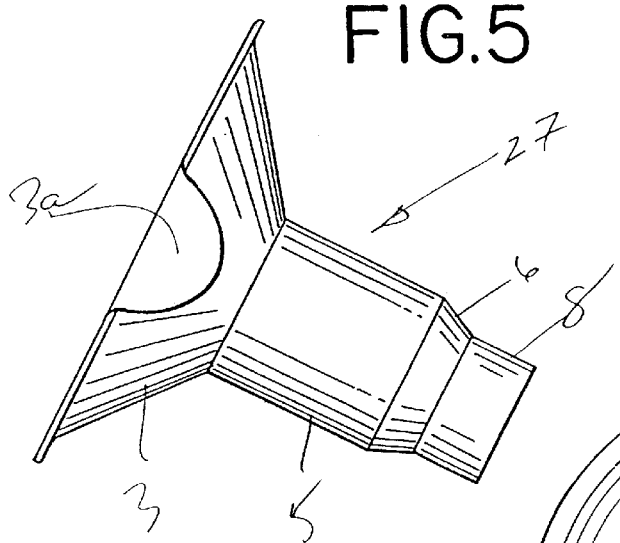
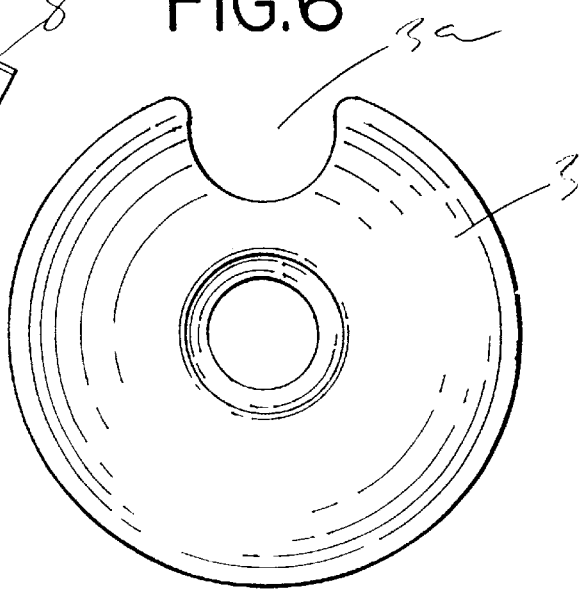

BREASTPUMP WITH UNIVERSAL HOOD BASE AND INTERCHANGEABLE SUCTION HOODS

This application is a divisional of application Ser. No. 09/450,404, filed on Nov. 29, 1999, now U.S. Pat. No. 6,387,072 the entire contents of which are hereby incorporated by reference, which claims benefit of Provisional No. 60/111,895 filed Dec. 10, 1998.

FIELD OF THE INVENTION

The present invention relates generally to breastpumps, and more particularly to a suction hood base for a breastpump, which can be used with a variety of different sized and shaped suction hoods (shields), such as having different internal diameters for the nipple-receiving portion, different nipple tunnel lengths, and the like, without the need for inserts or adapters, although the latter may also still be used for even greater versatility.

BACKGROUND OF THE INVENTION

Breastpumps are well known, and are generally comprised of a hood (or shield) that fits over the breast, a vacuum pump connected to the shield for generating an intermittent vacuum (or negative pressure) within the shield, and a receptacle for expressed milk. The intermittent suction action of the vacuum pump serves to pull on the breast and nipple and thereby extract milk in an action reminiscent of suckling. The extracted milk typically flows from the shield into a collection container for storage and later use. A breastpump of the foregoing type is shown in Larsson, U.S. Pat. No. 4,857,051, the disclosure of which is incorporated herein by reference.

In general, the suction hoods used with breastpumps are funnel shaped shields made of substantially rigid plastic. These hoods are quite durable and easily cleaned. It is also known that, in some instances, massaging the breast during pumping can aid in the extraction of milk from the breast. The rigid plastic shields do not massage the breast while the mother is pumping, because they are not flexible enough to do so.

In utilizing breastpumps, it has also been found that the wide variety in the size, shape, firmness and other variations in breasts and nipples gives rise to problems if a single size breast shield is to be given universal application. Shields used in connection with most breastpumps are nonetheless typically designed to handle a generalized breast and nipple.

Existing methods for altering the size of suction hoods have various disadvantages. For example, it is known to use a shield which includes at least one adjusting piece having a shape similar to that of the general funnel structure of the main funnel of the shield. The adjusting piece is insertable into the main shield, and effectively reduces the diameter of the funnel at its base, so that the hood can be conveniently used by women with smaller breasts or nipples.

It is therefore desirable to have a breatpump assembly that provides the ability to readily accommodate different size and shaped breasts and nipples. This would be useful both in manufacture as well as for the end user, and clinicians. It would also be desirable to have a breastpump which could accommodate specialty breast shields, such as breast shields having asymmetric form or other features that are adapted for particular problems, or seek to perform special results.

SUMMARY OF THE INVENTION

A principal objective of the present invention is to provide a breastpump, which can be used on a variety of different breasts without making operation of the breastpump more complicated by adding pieces or adapters. This objective is accomplished through the use of a single universal hood base and a set of different shields, all of which can be easily attached to the universal base. A significant advantage of the present invention is providing an appropriate fit and attendant comfort level for the mother, with ready adaptability for special situations, such as engorgement.

The suction hoods of the present invention generally are a funnel-shaped shield with a cylindrical portion extending downstream from the cone of the funnel. A universal hood base has a sleeve adapted for mating engagement with the cylindrical shaped portion of the shield. The shields of the present invention may vary in diameter length and angle (slope) in both the cone and the cylindrical part to accommodate a variety of different breasts and nipples. The diameter of the sleeve of the hood base, however, need not vary. Instead, the cylindrical portion of the shield is adapted to be inserted into, or alternatively fit over, the sleeve of the hood base to form a continuous press-fit seal, or interference fit. When using the breastpump, this seal allows a negative pressure to be established in the shield, which in turn pulls on the breast and nipple allowing expression of milk from the mother's breast.

In practice, a breastpump manufacturer may provide a pump assembly with a set of different shields. The mother can than try each different shield to determine which is most comfortable, and which one works most effectively for her. Moreover, if the mother's breasts change size or shape, such as through engorgement, during the period in which she is breast feeding her infant and using the breastpump, the mother can again try the different shields, one of which may be more comfortable and/or work more effectively.

Another object of the present invention is to provide an improved shield. In one embodiment the improved shield has a frame of relatively rigid plastic, which is integrally molded to a soft, flexible cone-shaped member. The flexible cone-shaped member of the shield is more comfortable to use for some mothers. Moreover, in use, the breast is primarily in contact with the cone-shaped member which contracts about and gently presses on the breast, allowing the breast to be massaged, and thereby aids in the expression of milk for some mothers.

In another embodiment of the improved breast shield, the foregoing soft flexible cone-shaped member is further provided with one or more thinned areas. These thinned areas are more flexible, and will be pulled more inwardly under negative pressure from the vacuum source. This yields localized regions of added massage. Such thinned flexible areas can also be provided on the cylindrical portions of the shield for massage of the nipple and surrounding breast.

The foregoing objects of the present invention will be further understood upon consideration of the following detailed description of the invention taken in conjunction with the accompanying drawings in which:

BRIEF DESCRIPTION OF THE DRAWINGS

FIG. 1 is an elevational view of two embodiments of a breastpump shield and a universal hood base in accordance with the present invention;

FIG. 2 is an enlarged sectional view of a shield in accordance with the present invention taken along line 2—2 of FIG. 1;

FIG. 3 is another embodiment similar to that of shield 1 of FIG. 1, but provided with thinned areas for massage.

FIG. 4 is an enlarged sectional view taken along line 4—4 of FIG. 3;

FIG. 5 is yet another embodiment of a shield specially adapted for use with breasts having regions which the shield is not desired to overlie, such as irritated or abscessed regions; and FIG. 6 is a front elevational view of the shield of FIG. 5.

DETAILED DESCRIPTION OF EMBODIMENTS OF THE INVENTION

The overall breastpump design used in conjunction with the present invention is generally shown in U.S. Pat. No. 4,857,051, and reference can be made to that patent for specific details of the breastpump and its operation. As seen in the accompanying FIG. 1, the breastpump apparatus or assembly has a suction hood or shield 1 and a hood base 7. Shield 1 has two parts. The first part 3 of shield 1 has a substantially wide cross-section (diameter) and is cone-shaped. During operation of the breastpump, cone 3 is placed over the breast of the user and serves as a receptacle for the breast. In that case, it need not be cone-shaped.

The second part 5 of shield 1 constitutes a generally cylindrical extension of a funnel, and has a cross-section (diameter) narrower than the cross-section of cone 3. During operation of the breastpump, cylindrical part end 8 of the hood is attached to base 7 through an interference fit, which allows communication between the cone 3 and the vacuum source 15 of the breastpump. Of course, a screw-on engagement, snap-fit or the like could also be used, but an interference fit is considered simple and desirable. This is particularly true if rotatability of the shield is desired, such as with an asymmetric shield construction.

In particular, hood base 7 is a universal base, which can be used in connection with a set of different shields having cones 3 and/or cylindrical parts 5 with varying diameters, shapes and angles, for instance. Base 7 has a hollow sleeve 9 adapted for mating engagement with the end 8 of the funnel. Base 7 also has some kind of connecting mechanism for attaching a first collar 11 to a vacuum source 12, and a second collar 13 to a collection container 14. In a preferred embodiment, collars 11 and 13 are screw-threaded for attachment to the vacuum source (e.g., a manual piston pump 15) and the collection container 14 (e.g., a plastic milk bottle) to create a seal.

As previously discussed, multiple sized shields for breast-pumps are needed because women have different breasts and nipples. A larger shield may be needed for women with larger nipples, for example. A larger shield will typically have a larger cone and a larger cylindrical part as well. Thus, the cylindrical part 5 of the larger shield may have a diameter that is greater than the interior diameter of the sleeve 9 of the hood base. As a result, the cylindrical end 8 of such an embodiment fits over the sleeve 9 of the hood base 7 to form the seal, rather than fitting within the sleeve 9.

As shown in FIG. 1, the diameter of cylindrical part 5 of shield 1 can be stepped down (made smaller) by forming a conical segment 6 on the cylindrical end downstream from the cone 3. The segment 6 adjoins the narrowed end 8 of cylindrical part 5. The end 8 has a diameter slightly less than that of sleeve 9 of the hood base, but widens slightly upstream to make the interference fit. Cylindrical part 5 could also simply gradually taper inwardly downstream to a diameter slightly less than the interior diameter of sleeve 9. This decrease in diameter of cylindrical part 5 allows the cylindrical end 8 to be inserted into sleeve 9 to form a substantially airtight continuous press-fit seal or interference fit upstream from end 8 with the interior wall of sleeve 9 (see FIG. 1 phantom line 16). When the breastpump is operated, this press-fit seal allows a negative pressure (vacuum) to be established in shield 1. The negative pressure in the shield then pulls on the breast and nipple, causing milk to be expressed.

As will be appreciated by those skilled in the art, a smaller shield may have a cylindrical part 5 with a diameter that is smaller than that of the interior diameter of sleeve 9. In such a situation, the cylindrical part 5 of the smaller shield would have an increasing wall thickness upstream to an outside diameter that would engage with the interior of sleeve 9.

As further shown in FIG. 1, another shield 2 has a cylindrical part 5' (primed numbers indicate similar structure to their nonprimed counterparts) with an interior diameter that is larger than the interior diameter of sleeve 9. Cylindrical part 5' of shield 2 therefore is designed to fit tightly over the exterior of sleeve 9, and forms a press-fit seal or interference with the exterior wall of sleeve 9. A taper is provided to the interior of the cylindrical part 5' which gradually reduces its interior diameter to engage with the outside of the sleeve 9, as at end 8.

Those skilled in the art will also appreciate that there are other ways to attach the shield to the universal base so that the necessary seal is formed. For instance, the sleeve 9 could be inwardly tapered, and the cylindrical parts 5, 5' untapered. Again, the cylindrical end 8 of the shield may be attached to the sleeve of the hood base through a threaded engagement. Alternatively, the cylindrical end of the shield and the sleeve of the base may be attached through the use of a snap-fit. A snap-fit can be made by forming a bead around the top edge of the sleeve of the hood base, which would be received in an annular recess formed in the cylindrical end. An intermediate coupling element could also be used. These and other alternative attachment methods permit easy and quick removal of the shield from the hood base.

Yet another aspect of this invention is in the improved shield illustrated by shield 2 in FIG. 1. Shield 2 comprises a relatively rigid frame having a tubular-shaped extension 17 and a ring 19. The extension 17 and ring 19 are connected by rigid arms or struts 23, which serve to keep the ring 19 spaced from the extension 17. The remainder of the funnel of shield 2 is a soft, elastic material. The soft funnel shaped membrane 21 can be formed from a thermoplastic elastomer, rubber, latex or silicone. As shown in the cross-section taken along line 2—2 in FIG. 2, the membrane 21 is integrally molded to the interior wall of the ring 19. In this preferred embodiment, funnel shaped membrane 21 is likewise integrally molded to the interior of extension 17, and extends above the outermost edge 25 of ring 19.

Support members 23 also form loops on the sides of shield 2. A strap may be placed through the support members and the underlying membrane 21 so that the mother can strap the assembly onto her breast during pumping leaving her hands free to attend to her infant. Various methods for supporting a breastpump shield assembly on a woman's breast are disclosed in U.S. Pat. No. 5,514,166 assigned to Medela, Inc. Reference can be made to that patent for specific details on how to support a shield assembly on a woman's breast.

In use, the shield 2 is lightly pressed over the breast while operating the pump. A negative pressure is intermittently generated in the shield 2. When the shield is applied to the breast and a negative pressure is developed within the shield, the flexible cone part of the shield (membrane 21) is drawn inwardly against the breast; when the negative pressure is reduced, the flexible funnel releases. This action of the flexible funnel causes the breast to be massaged during pumping, thereby aiding in the expression of the mother's milk.

A variation of the embodiment of shield 2 is shown in FIGS. 3 and 4. This latter embodiment has thin-walled areas formed in the funnel-shaped membrane 21 as well as in the cylindrical extension 17. Shield 2' thus has a thinned area 21a shown in the membrane 21; in actuality, there could be multiple such thinned areas 21 spaced around the cone of this shield 2'. In similar fashion, another thinned area 17a is provided in the extension 17 (thinned area 17a being integrally molded with the rigid plastic extension 17 in the manner previously described). There could likewise be multiple such thinned areas 17a around the extension.

Under vacuum, the thinned areas 21a and 17a will be pulled inwardly by the negative pressure within the shield 2'. In the case of the areas 21a, this will be even more pronounced than the surrounding flexible material of the membrane 21. This serves to provide regions of localized breast massage with respect to the areas 21a, and nipple massage insofar as the areas 17a. As with the other shields 1 and 2, shield 2' can be provided as part of a set of shields, or made available separately as a specialty attachment. It can also be made as a fixed shield (i.e., formed integral with the hood base in manufacture), while still yielding the unique structure for massage, although not the interchangeability desired in another aspect of the invention. There may be other ways, besides a thinned area, provided on the breast shield to yield the same concept of a movable portion to provide localized pressure for massage.

Turning to FIGS. 5 and 6, yet another embodiment of an improved breast shield is illustrated. This shield 27 is again made interchangeable in keeping with that aspect of the present invention, although it need not be made so. However, releasable attachment of this shield 27 is considered most desirable because of the cut-out area 3a that is provided in the cone 3. This cut-out 3a is useful for conditions of the breast that make it uncomfortable or otherwise undesirable to have the cone 3 overlying the breast at a particular spot. This could occur with an abscess or the like on the breast. The interchangeable nature of the shield 27 would thus enable its ready use with a common hood base 7 when needed, while also allowing rotatability of the shield 27 on the base 7, so that the shield can be properly oriented as required.

Thus, while the invention has been described with reference to certain embodiments, those skilled in the art will recognize modifications of structure, arrangement, composition and the like can be made with respect to the present invention, yet fall within the scope of the invention as hereafter claimed.

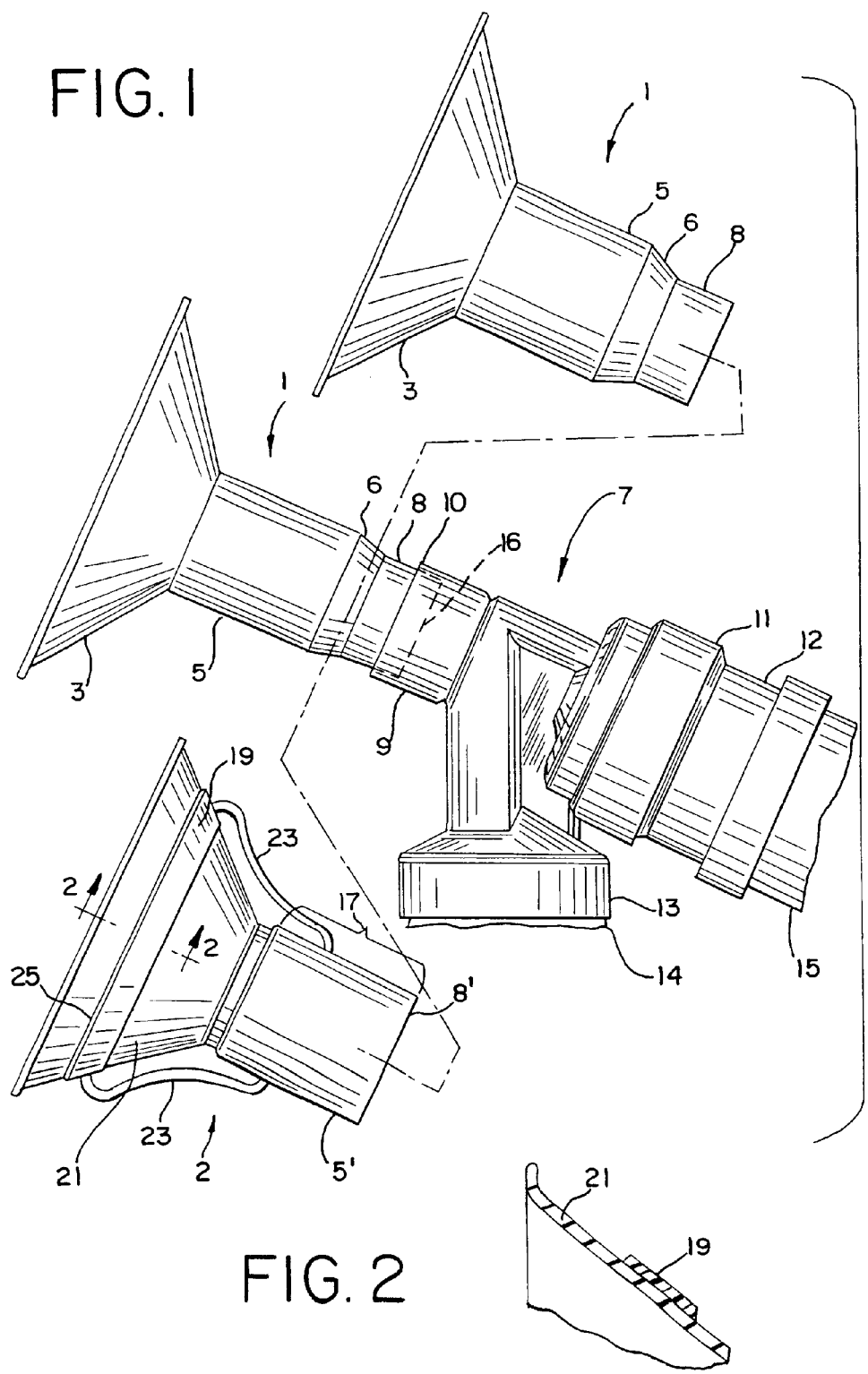

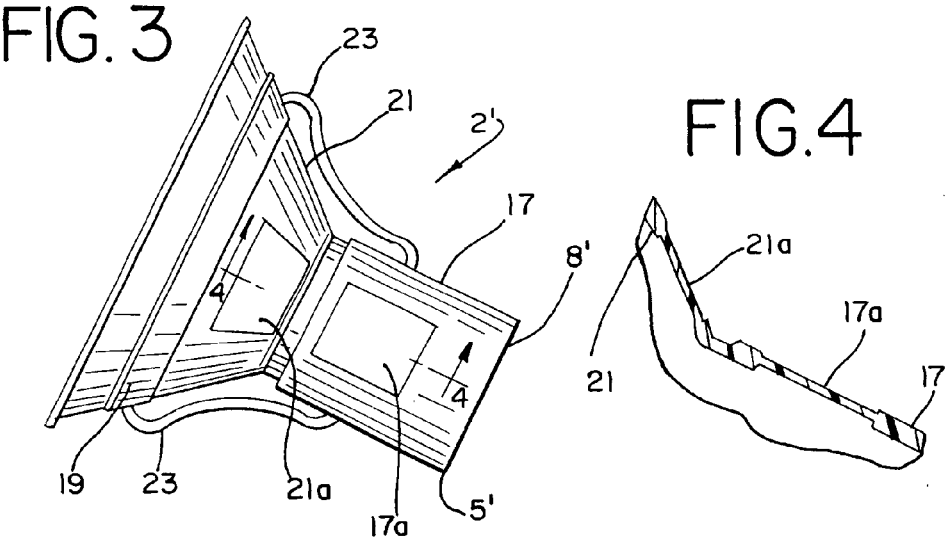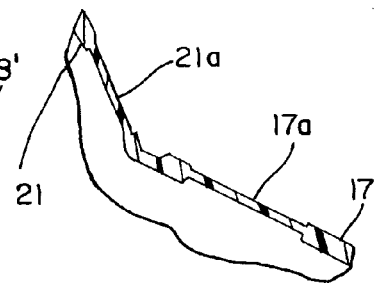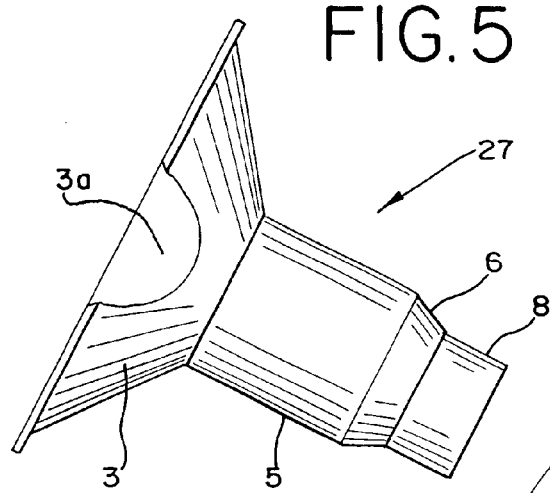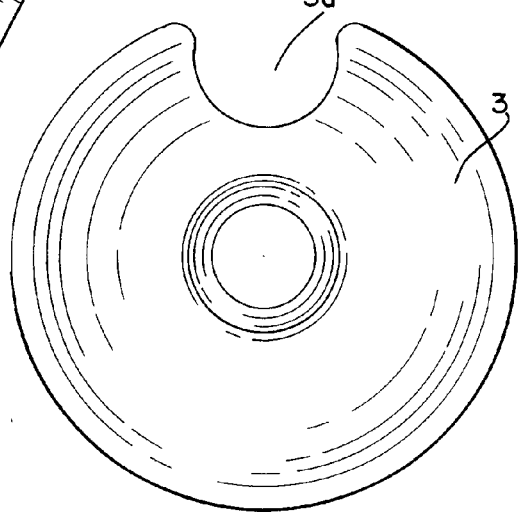

What is claimed is:

1. A breastpump for mother's milk, comprising:
   a suction hood base having a sleeve part;
   at least first and second breast shields, each breast shield having a breast receptacle part and a tubular part extending downstream from said receptacle part, said tubular part of said first breast shield having a different sized internal diameter than said tubular part of said second breast shield, wherein said at least first and second breast shields are interchangeable;
   a connecting mechanism adapted to form a substantially airtight seal between a respective breast shield and said hood base sleeve part;
   a milk receptacle for collecting breastmilk expressed into a respective breast shield;
   a conduit structure conveying expressed breast milk from said tubular part to said milk receptacle;
   a pump mechanism for creating a periodic reduced air pressure; and
   a vacuum connection for conveying said reduced air pressure to a respective breast shield.

2. The breastpump of claim 1 wherein said sleeve part has an interior sidewall and an exterior sidewall, and at least one tubular part is tapered along its exterior to fit within said sleeve part and engage with said sleeve part interior sidewall to form a substantially airtight fit with said sleeve part interior sidewall.

3. The breastpump of claim 2 wherein at least one tubular part is tapered along its interior to fit over said sleeve part exterior sidewall and engage with said sleeve part exterior sidewall to form a substantially airtight fit with said sleeve part exterior sidewall.

4. The breastpump of claim 1 wherein said breast receptacle part of said first breast shield has a different shape from said breast receptacle part of said second breast shield.

5. The breastpump of claim 4 wherein said tubular part of said first breast shield has a different radial cross-sectional shape from said tubular part of said second breast shield.

6. The breastpump of claim 1 wherein one of said breast receptacle part and said tubular part of said first breast shield is made of a different material from its corresponding part of said second breast shield.

7. A breastpump for mother's milk, comprising:
   a suction hood base;
   at least first and second breast shields, each breast shield having a breast-receiving part and a tubular part extending downstream from said breast-receiving part, at least one of said breast-receiving part and said tubular part of said first breast shield having at least one of a different size and shape from said breast-receiving part of said second breast shield, wherein said at least first and second breast shields are interchangeable for providing the breastpump with a plurality of adaptations in the form of different breast shields;
   a connecting mechanism adapted to form a substantially airtight seal between a respective breast shield and said suction hood base;
   a receptacle for collecting breastmilk expressed into a respective breast shield;
   a conduit structure conveying expressed breast milk from said tubular part to said receptacle;
   a pump mechanism for creating a periodic reduced air pressure; and
   a vacuum connection for conveying said reduced air pressure to a respective breast shield, wherein said tubular part of said first breast shield has a different internal diameter than that of said tubular part of said second breast shield.

8. The breastpump of claim 7 wherein said breast-receiving part of said first breast shield has a different size than that of said breast-receiving part of said second breast shield.

9. The breastpump of claim 7 wherein one of said breast receiving part and said tubular part of said first breast shield is made of a different material from its corresponding part of said second breast shield.

10. An improved breastpump assembly kit for the expression of mother's milk, comprising:
    a suction hood base;
    at least first and second interchangeable breast shields, each breast shield having a funnel shape with a cone part and a tubular part extending downstream from said cone part, said first breast shield having a different structure from that of said second breast shield, for providing the breastpump with a plurality of adaptations in the form of different breast shields; and a releasable connecting mechanism forming a substantially airtight seal between a respective breast shield and said hood base, wherein said tubular part of said first breast shield has a different internal size than that of said tubular part of said second breast shield.

11. The improved breastpump assembly kit of claim 10 wherein said cone part of said first breast shield has a different shape from said cone part of said second breast shield.

12. An improved breastpump assembly kit for the expression of mother's milk, comprising:

a suction hood base;

at least first and second interchangeable breast shields, each breast shield having a funnel shape with a cone part and a tubular part extending downstream from said cone part, said first breast shield having a different structure from that of said second breast shield, for providing the breastpump with a plurality of adaptations in the form of different breast shields; and a releasable connecting mechanism forming a substantially airtight seal between a respective breast shield and said hood base, wherein said cone part of one of said at least first and second interchangeable breast shields has a cut-out portion, and said breast shield with said cut-out portion is rotatably mounted on said hood base.

13. An improved breast shield for a breastmilk pump assembly, wherein the improvement comprises: a conical part of said breast shield for receiving a breast therein, said conical part having a cut-out portion which extends a distance from a periphery of said conical part border thereof, said distance being less than half of a diameter of said conical part, wherein said cut-out portion avoids contact of the breast by said conical part in use of the breast shield.

14. The improved breast shield of claim 13 wherein said breastmilk pump assembly includes a hood base, and wherein the improvement further comprises a connecting mechanism for said breast shield rotatably mounting said conical part to said hood base.

* * * * *

UNITED STATES PATENT AND TRADEMARK OFFICE
CERTIFICATE OF CORRECTION

PATENT NO. : 6,723,066 B2
DATED : April 20, 2004
INVENTOR(S) : Larsson et al.

It is certified that error appears in the above-identified patent and that said Letters Patent is hereby corrected as shown below:

Drawings, "informal Figs. 1-6" are replaced with -- formal Figs. 1-6 -- as shown on the attached pages.

Signed and Sealed this

Fourteenth Day of September, 2004

JON W. DUDAS
*Director of the United States Patent and Trademark Office*